US012458412B2

United States Patent
Lewis et al.

(12) United States Patent
(10) Patent No.: US 12,458,412 B2
(45) Date of Patent: Nov. 4, 2025

(54) SACROILIAC FUSION IMPLANT

(71) Applicants: Adam Isaac Lewis, Madison, MS (US); Lauren Chase Thornburg, Cumming, GA (US)

(72) Inventors: Adam Isaac Lewis, Madison, MS (US); Lauren Chase Thornburg, Cumming, GA (US)

( * ) Notice: Subject to any disclaimer, the term of this patent is extended or adjusted under 35 U.S.C. 154(b) by 66 days.

(21) Appl. No.: 18/425,691

(22) Filed: Jan. 29, 2024

(65) Prior Publication Data

US 2025/0241688 A1 Jul. 31, 2025

(51) Int. Cl.
*A61B 17/70* (2006.01)
*A61B 17/17* (2006.01)
*A61F 2/30* (2006.01)

(52) U.S. Cl.
CPC ...... *A61B 17/7055* (2013.01); *A61B 17/1757* (2013.01); *A61F 2/30988* (2013.01); *A61F 2002/30995* (2013.01)

(58) Field of Classification Search
None
See application file for complete search history.

(56) References Cited

U.S. PATENT DOCUMENTS 6,730,127 B2 5/2004 Michelson
7,648,509 B2 1/2010 Stark
8,454,618 B2 6/2013 Stark
8,734,456 B2 5/2014 Stark
9,351,847 B2 5/2016 Reed et al.
9,603,713 B2 3/2017 Moskowitz et al.
9,808,346 B2 11/2017 Stark
10,117,691 B2 11/2018 Predick
10,117,750 B2 11/2018 Predick
10,149,764 B2 12/2018 Stark
10,278,742 B2 5/2019 Pavlov et al.
11,076,967 B2 8/2021 Reed et al.
11,083,511 B2 8/2021 Schifano et al.
11,376,026 B2 7/2022 Donner et al.
2005/0049590 A1* 3/2005 Alleyne .................. A61F 2/442 606/279
2006/0155297 A1* 7/2006 Ainsworth ............ A61F 2/4425 606/99
2013/0076180 A1* 3/2013 Park ........................ H02K 7/085 310/90
2013/0226300 A1* 8/2013 Chataigner ........... A61F 2/4455 623/17.16
2022/0409393 A1* 12/2022 Ashleigh ............... A61F 2/4611

* cited by examiner

*Primary Examiner* — Tessa M Matthews
(74) *Attorney, Agent, or Firm* — David O. Simmons

(57) ABSTRACT

A sacroiliac fusion implant device assembly has an implant body with a sliding block and a pair of movable bone spikes. The distal end has a tapered end with an opening configured to receive a guide pin during insertion into a joint between a sacrum and an ilium, and the proximal end has a cannulated threaded post configured to receive a guide pin and to move a sliding block. The sliding block is movable from a retracted unlocked position and to a deployed locked position when moved toward the distal end as the threaded post is rotated clockwise. The bone spikes are movable from a retracted position in the implant body to an exposed deployed locked position by moving the sliding block which presses the spikes up and out of the retracted position extending the bone spikes into bone in the sacroiliac joint.

9 Claims, 9 Drawing Sheets

SACROILIAC FUSION IMPLANT

FIELD OF THE INVENTION

The present invention relates to a novel sacroiliac fusion implant device.

BACKGROUND OF THE INVENTION

The sacroiliac or SI joint is a very important joint in the lower back with one joint on each side of the pelvis basically connecting the base of the spine to the pelvis. The sacroiliac joint is a low-motion joint that connects the hip bones to either side of the sacrum. It is formed by the tailbone, sacrum, and waist bones, ilium, and functions as a shock absorber between the spine and legs. It is a generally C shaped joint with cartilage and an extensive complex of supporting ligaments.

One of the functions of the SI joint is a shock absorber. It transfers the forces from the upper body to the lower body. As such it is susceptible to injury which can impact its ability to act as a shock absorber. Causes of SI joint injury include trauma, degeneration, inflammation, pregnancy, ligament laxity, and muscle weakness.

The standard surgery used to address SI joint pain is sacroiliac joint fusion to completely eliminate movement at the sacroiliac joint by grafting together the ilium and sacrum. Sacroiliac fusion involves the use of implanted screws or rods, as well as a possible bone graft across the joint. Minimally-invasive procedures have been developed in recent years that improve outcomes in pain and disability, and reduce recovery time. Joint fusion can effectively reduce pain and instability caused by sacroiliac joint dysfunction or inflammation, sacroiliitis.

The present invention as described herein discloses a unique implant design that improves SI joint fusion.

SUMMARY OF THE INVENTION

A sacroiliac fusion implant device assembly has an implant body with a sliding block and a pair of movable bone spikes. The implant body has a distal end and a proximal end with a longitudinal axis extending between a center of the distal end and a center of the proximal end. A pair of sidewalls connects the distal and proximal ends. The distal end has a tapered end with an opening configured to receive a guide pin during insertion into a joint between a sacrum and an ilium, and the proximal end has a cannulated threaded post configured to receive a guide pin and to move a sliding block. The sliding block is positioned in the implant body and held to the threaded post. The sliding block is movable from a retracted unlocked position and to a deployed locked position when moved toward the distal end as the threaded post is rotated clockwise. The pair of movable bone spikes is held in opposing sides of the implant body. Each bone spike is held in a pocket of the implant body. One first pocket is open at a first surface of the implant body and a second pocket is open at an opposing second surface of the implant body. The bone spikes are movable from a retracted position in the implant body to an exposed deployed locked position by moving the sliding block which presses the spikes up and out of the retracted position extending the bone spikes into bone in the sacroiliac joint.

The sacroiliac fusion implant device assembly further has a pair of locking cleats on the sliding block engaging sidewalls of the implant body when the threaded post is rotated into the implant body proximal end. The locking cleats of the sliding block align with a protrusion on the sidewall of the implant body to help prevent the bone spikes from being moved back to the retracted position and to alert the surgeon that the threaded post has reached the fully inserted position with the bone spikes deployed.

Each of the bone spikes has a curved groove extending along a portion of the side of the bone spike that moves over the protrusion following a curvilinear path to the deployed locked position as the sliding block presses against the bone spike.

Each of the pair of bone spikes is curvilinear and has a positive stop at the proximal end of the bone spike to help prevent over deployment.

The first exterior surface and the second exterior surface have a plurality of gripping ridges configured to engage bone or tissue upon implantation, wherein the plurality of gripping ridges are inclined from the distal end towards the proximal end at an angle of 45 degrees or less.

The implant body is manufactured by traditional machining techniques or 3D printed using implantable grade materials. The implant body can be made of titanium.

In one embodiment, the sacroiliac fusion implant device assembly has dimensions of 9 mm height, 14 mm width and 28 mm length at the distal end with a range of a 0 degree to 7 degree inclination toward the proximal end.

The sacroiliac fusion implant device assembly may be offered in a reusable or disposable instrument/implant set.

A method of implanting a sacroiliac fusion implant device into a sacroiliac joint, the method comprises: providing an implant fusion device according the present invention; inserting the implant fusion device into a space between the sacrum and the ilium with an insertion tool connected to the threaded post to a desired depth; rotating the threaded post using the insertion tool to move a pair of bone spikes from a retracted position held in pockets of the implant body to a deployed position causing the spikes to penetrate into the bones of the sacrum and the ilium one on each side of the implant body, thereby locking the implant device in the joint, and wherein the threaded post is rotated until the proximal end of the threaded post is moved inside the implant body at the proximal end.

BRIEF DESCRIPTION OF THE DRAWINGS

The invention will be described by way of example and with reference to the accompanying drawings in which.

DETAILED DESCRIPTION OF THE INVENTION

With reference to FIGS. 1-13, a sacroiliac fusion implant device is illustrated according to the present invention. The implant device features an internally threaded sliding block that pushes two opposing bone spikes in a curvilinear motion. This movement of the spikes is created by a pushing action on an exposed threaded post which is rotated creating a linear force which is placed on the sliding block which in turn presses the spikes at a proximal end directing the spikes up and out of their retracted position within the implant body. Once the threaded post is fully hidden, two internal locking cleats on the side of the sliding block engage with the lateral walls or sidewalls of the implant to assist in securing the expanded position of the spikes. The locking cleat feature provides a dual locking mechanism for the shims to prevent the possibility of inadvertent retraction of the spikes and the implant body once it is fully implanted in the sacroiliac. Each spike has a positive internal stop to prevent over deployment.

The curvilinear spikes are guided by internal pockets as well as internal pins to ensure they traverse the correct pathway. The implant body is also cannulated to be delivered over a guide wire or Steinmann Pin.

Generally, the implant device has dimensions of 9 mm height×14 mm width×28 mm length with 7 degrees of lordosis although larger or smaller sizes may be offered with varying degrees of lordosis including a 0-degree parallel implant.

Figure 1:
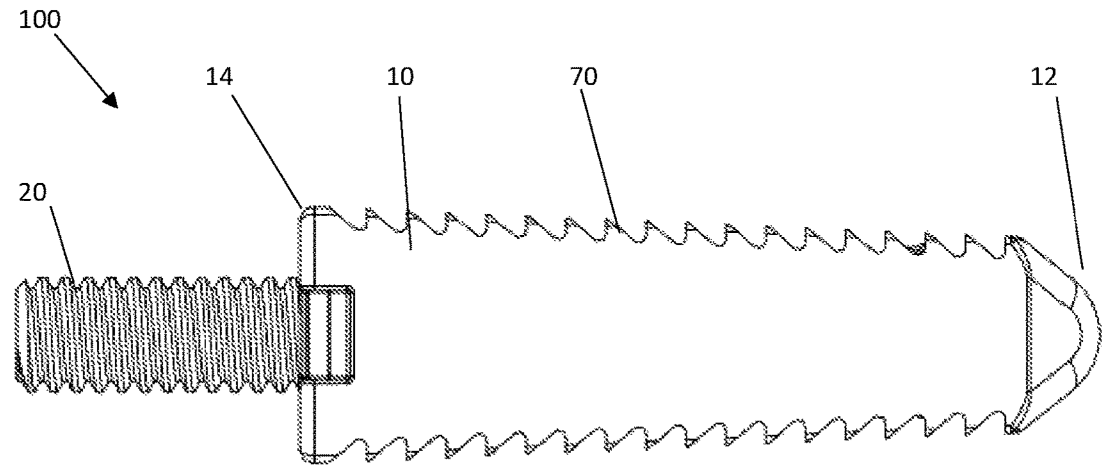
FIG. 1 is a side view of the SI fusion device of the present invention in a retracted position.
Figure 2:
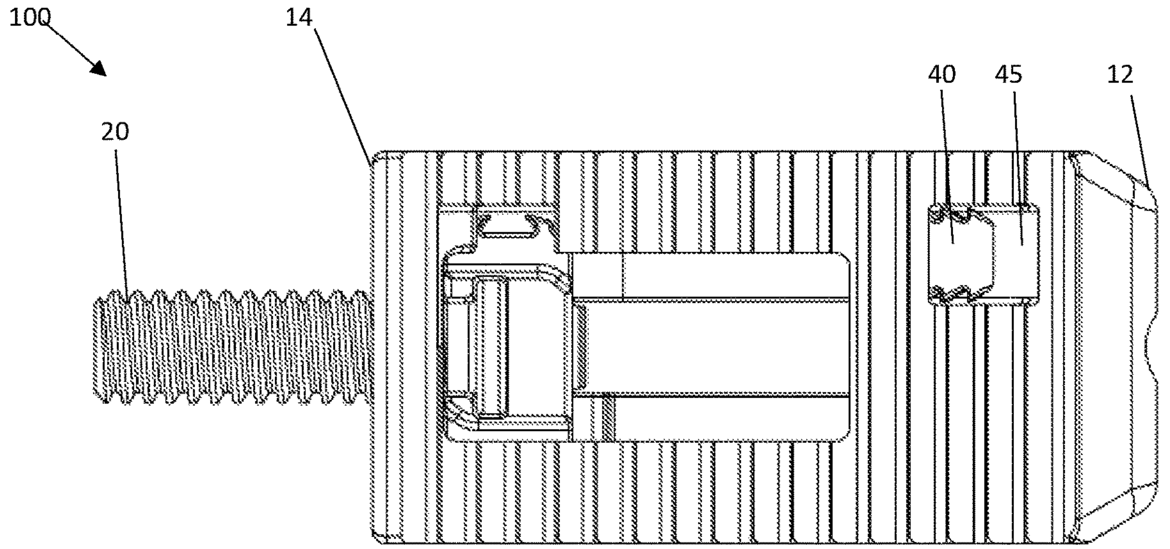
FIG. 2 is a top view of the SI fusion device of the present invention in a retracted position.

With reference to FIGS. 1 and 2, the implant device assembly 100 is illustrated with the threaded post being secured to the proximal end 14 of the implant body 10. A distal end 12 of the implant body 10 is illustrated with a curved or arched leading end which is illustrated in FIG. 2 is slightly narrower than the overall width of the implant body 10 providing a slight taper at the implant distal end 12 to assist in implantation into the SI joint. As illustrated the threaded post 20 is connected to a sliding block 30, as the threaded post 20 is rotated it moves from the proximal retracted position towards a distal direction which moves the spikes 40 held in pockets 45 held in each side of the implant body 10 in a direction that allows the spikes 40 to extend and be exposed outward of the inside of the implant body surface. The implant body 10 has a first exterior surface 15 with a plurality of ridges 70 and a second exterior surface 16 with a plurality of ridges 70. These ridges 70 provide bone gripping surfaces that upon implantation easily slide into the joint, but resist movement out of the joint due to the gripping action and the slope of the ridges 70 as illustrated. Ideally, the implant body 10 has a longitudinal axis centered on the implant body that passes through an opening at the distal end 12 directly towards the proximal end 14, the threaded post 20 is cannulated such that the implant body 10 can be passed over the guide pin on insertion. As illustrated in FIG. 2, the first exterior surface 15 of the implant body 10 shows a pocket 45 with a portion of the spike 40 shown retracted lying in the pocket 45.

Figure 3:
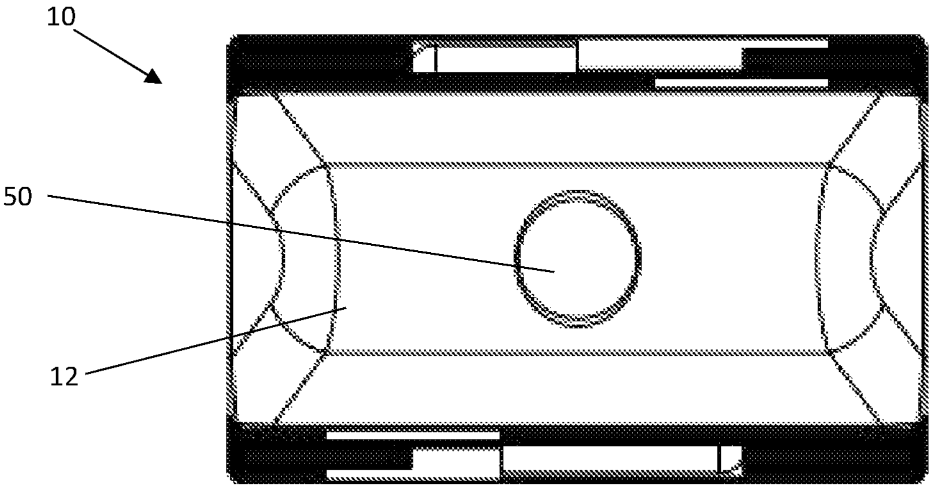
FIG. 3 is a distal end view of the SI fusion device of the present invention in a retracted position.

FIG. 3 illustrates the distal end 12 of the implant body 10, as shown, the central opening 50 coincident with the longitudinal axis.

Figure 4:
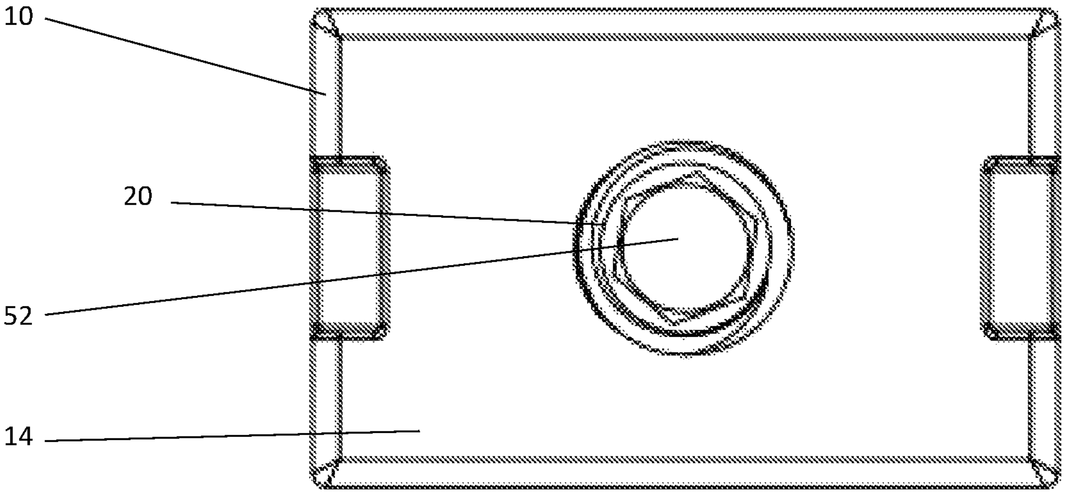
FIG. 4 is a proximal end view of the SI fusion device of the present invention in a proximal position.

FIG. 4 shows the proximal end 14 with the threaded post 20 being cannulated in such a fashion that it creates an opening 52 at the proximal end 14 for receiving a guide pin.

Figure 5:
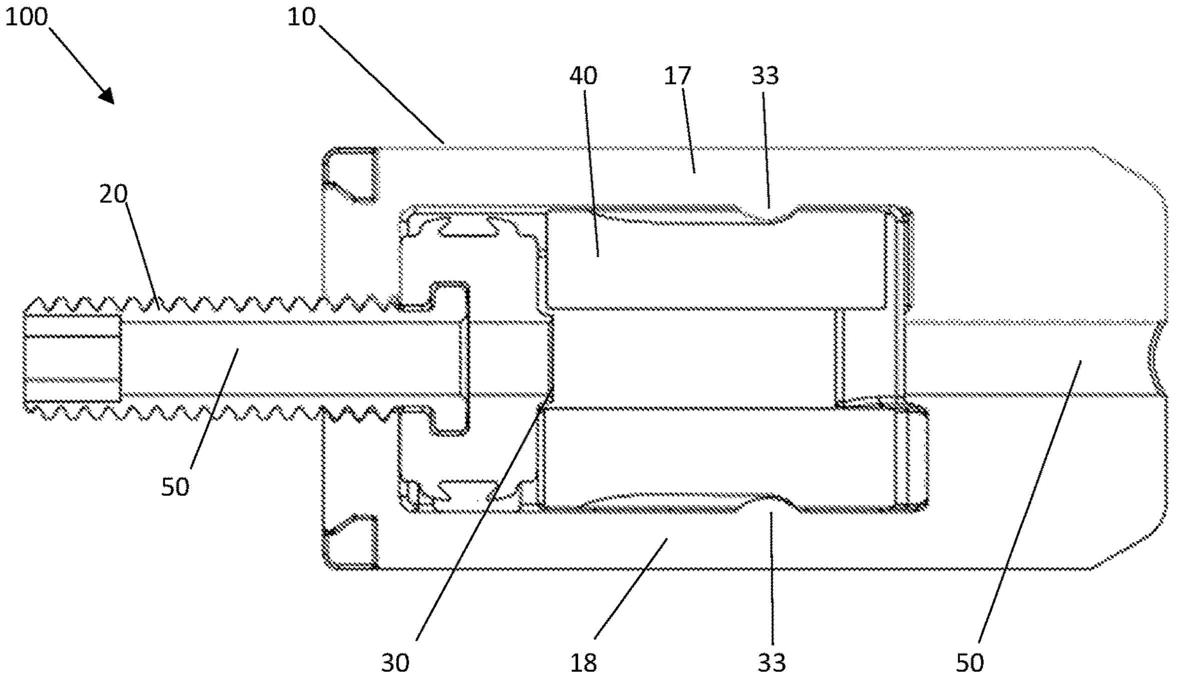
FIG. 5 is a cross sectional view of the SI fusion device of the present invention in a retracted position.
Figure 6:
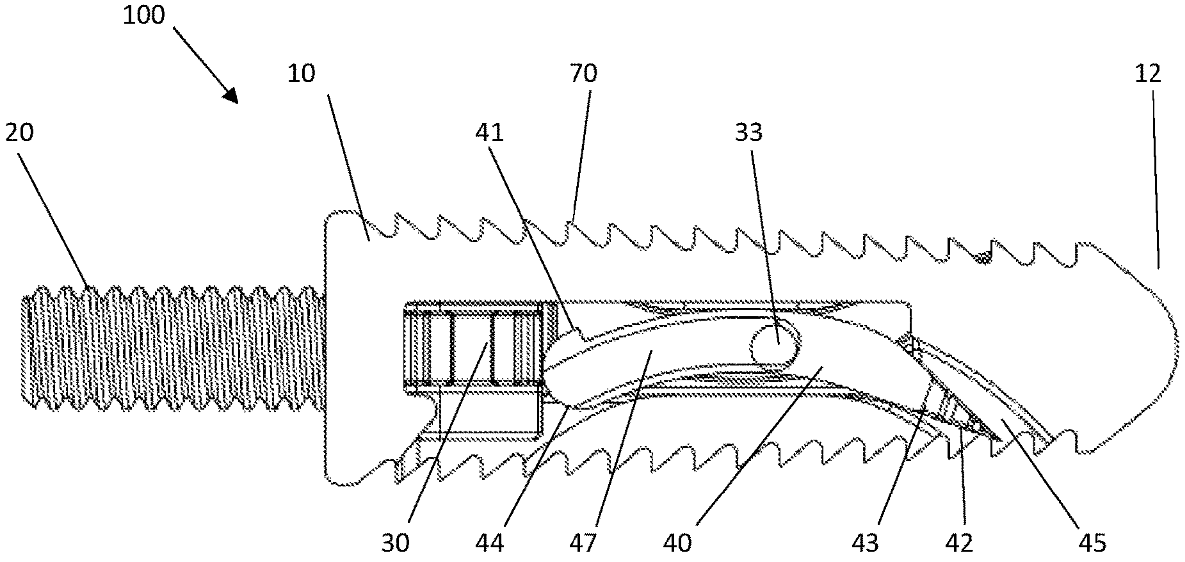
FIG. 6 is a cross sectional view of the SI fusion device of the present invention in a retracted position.
Figure 7:
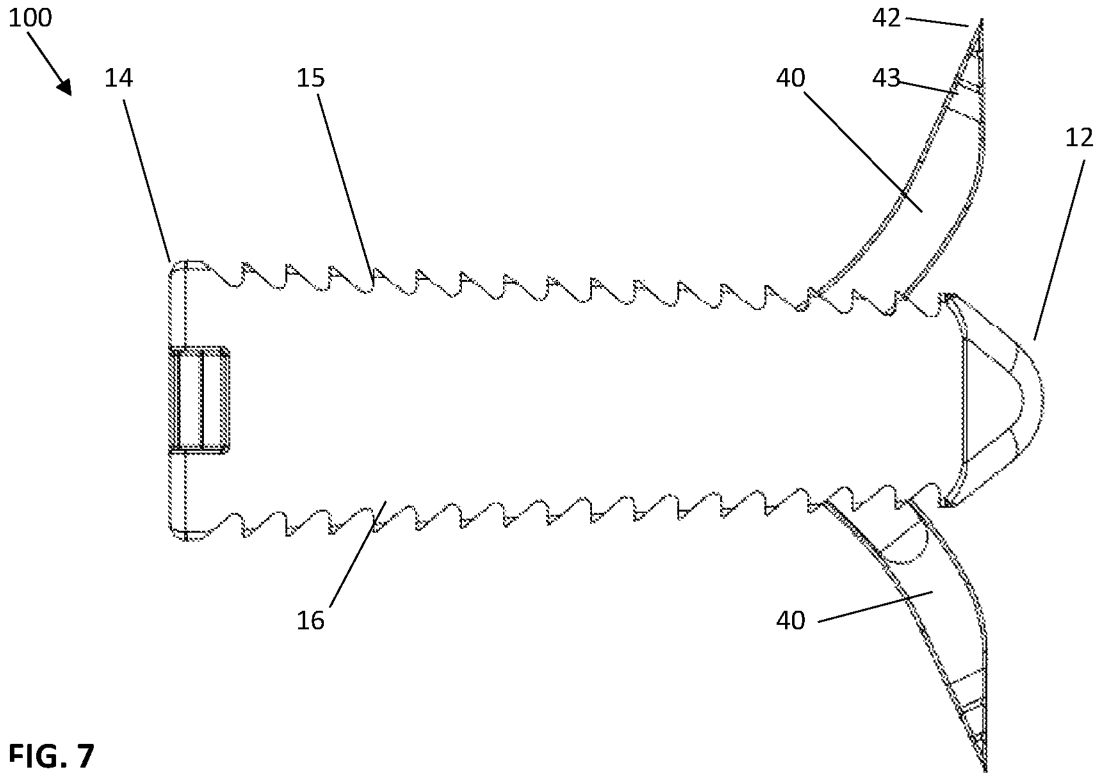
FIG. 7 is a cross-sectional view of the SI fusion device in a deployed position.
Figure 8:
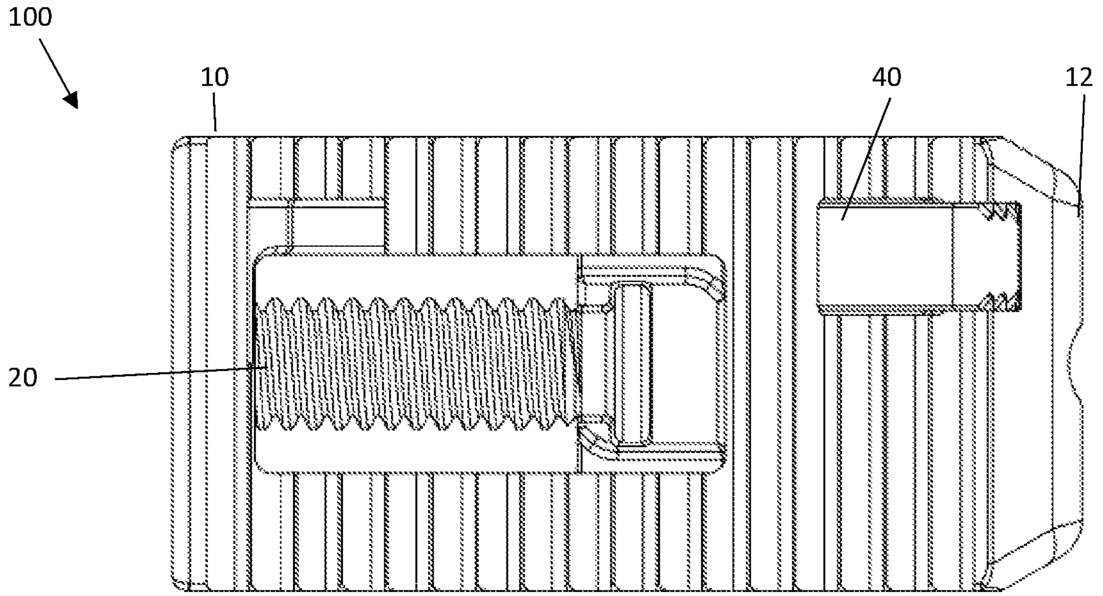
FIG. 8 is a top view of the SI fusion device in a deployed position.

FIG. 5 is a cross-sectional view that illustrates this feature of the cannulated opening in the implant body through the treaded post 20 and shows the sliding block 30 assembly that allows the spikes 40 lying with the pockets 45 of the implant body 10 to be pushed. This is best illustrated in FIG. 6, wherein the threaded post 20 is abutting a proximal end of the spike 40. As shown, the spike 40 has a curvilinear groove 47 that moves over the protrusion 33 to assist in guiding the spikes. The groove 47 is central to the spike 40, the spike 40 has a distal end 42 with a plurality of protrusions 43. The spike distal end 42 comes to a sharp point and has the protrusions 43 configured such that as the spike 40 is pushed by the threaded post 20, as shown in FIG. 7, outwardly into the fully deployed position, the spikes 40 engage bond and lock the implant device 100 into the joint with one spike 40 on each side of the joint penetrating into the bone and thereby locking the implant device 100 into the joint. When this occurs, as shown in FIGS. 7 and 8, the threaded post 20 is fully hidden and rotated such that it is entirely inside the implant body 10.

Figure 9:
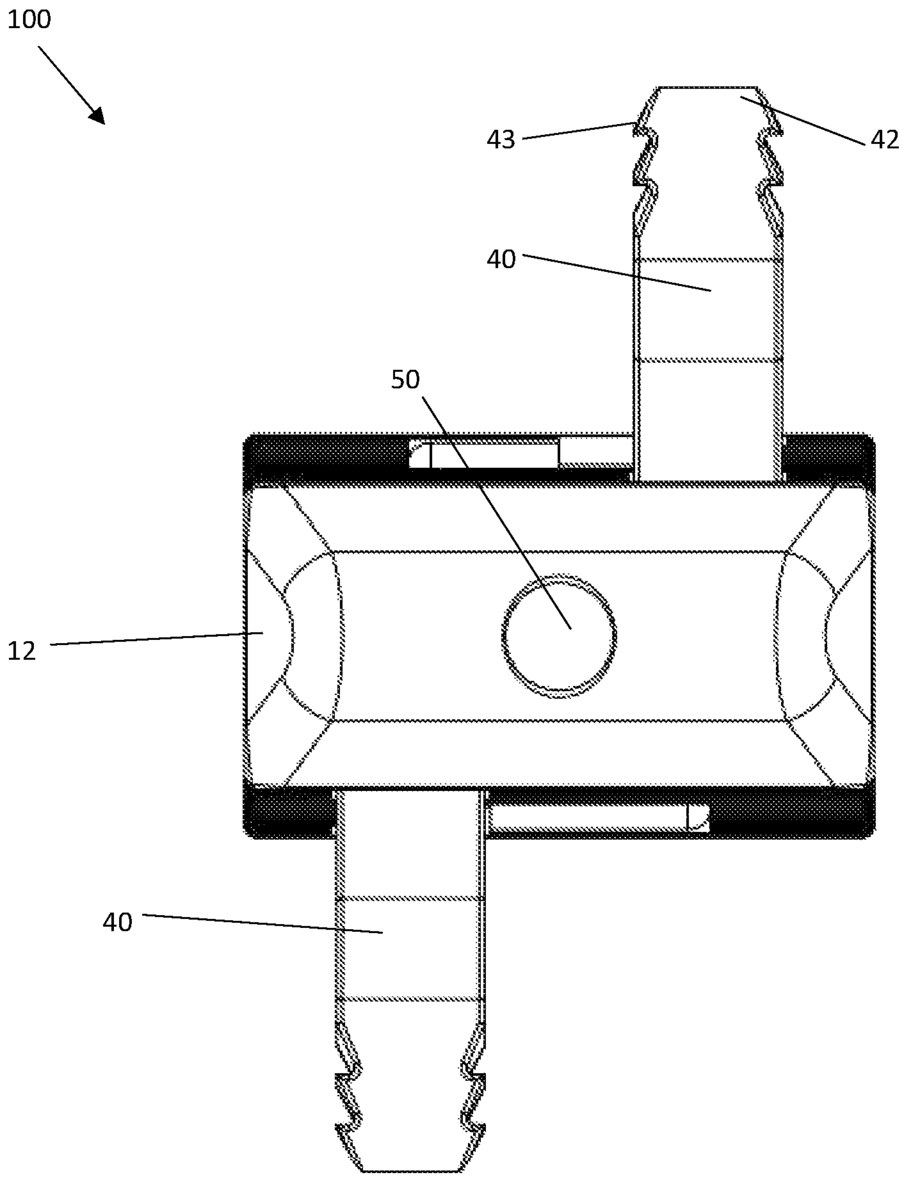
FIG. 9 is distal end view of the SI fusion device in a deployed position.

FIG. 9 shows in greater detail how the spikes 40 have the projections or prongs 43 at the sharp spike distal end 42 in the exposed or deployed position, as shown from a distal end perspective.

Figure 10:
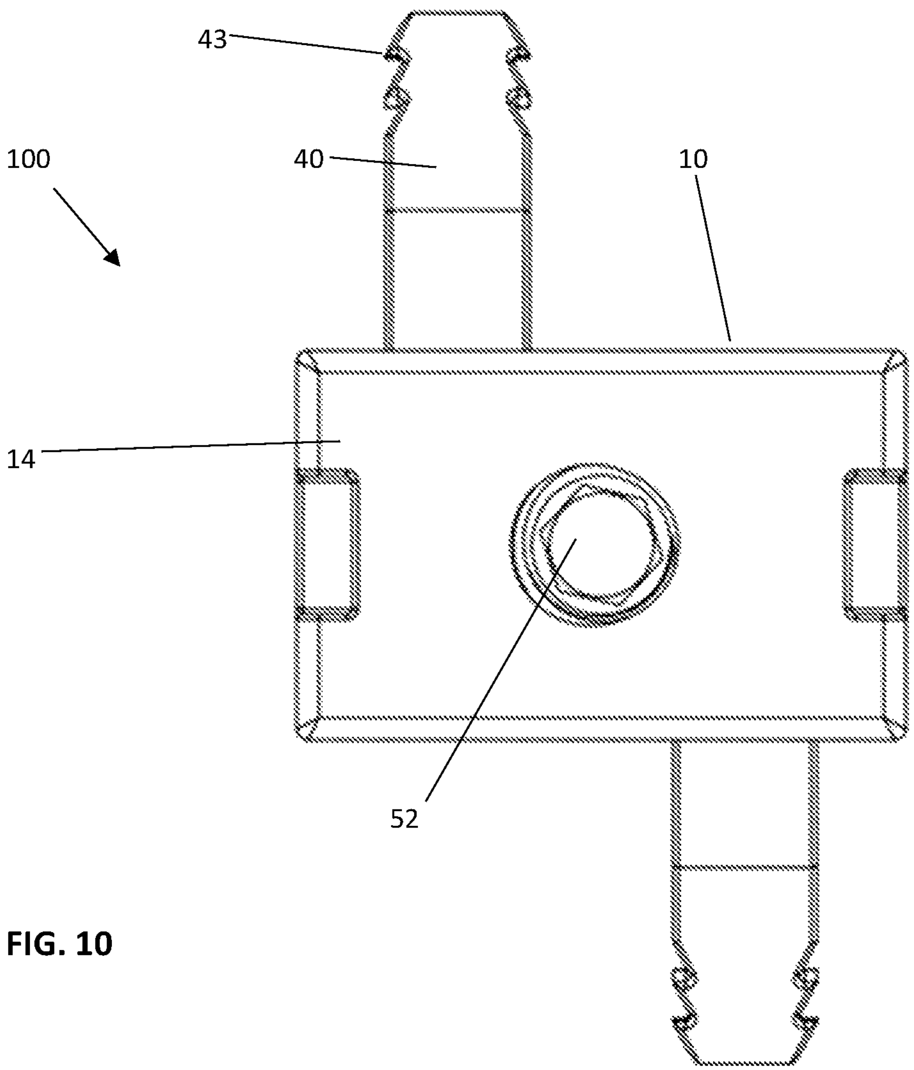
FIG. 10 is a proximal end view of the SI fusion device in a deployed position.

FIG. 10 shows the spikes 40 from a proximal end 12 position.

Figure 11:
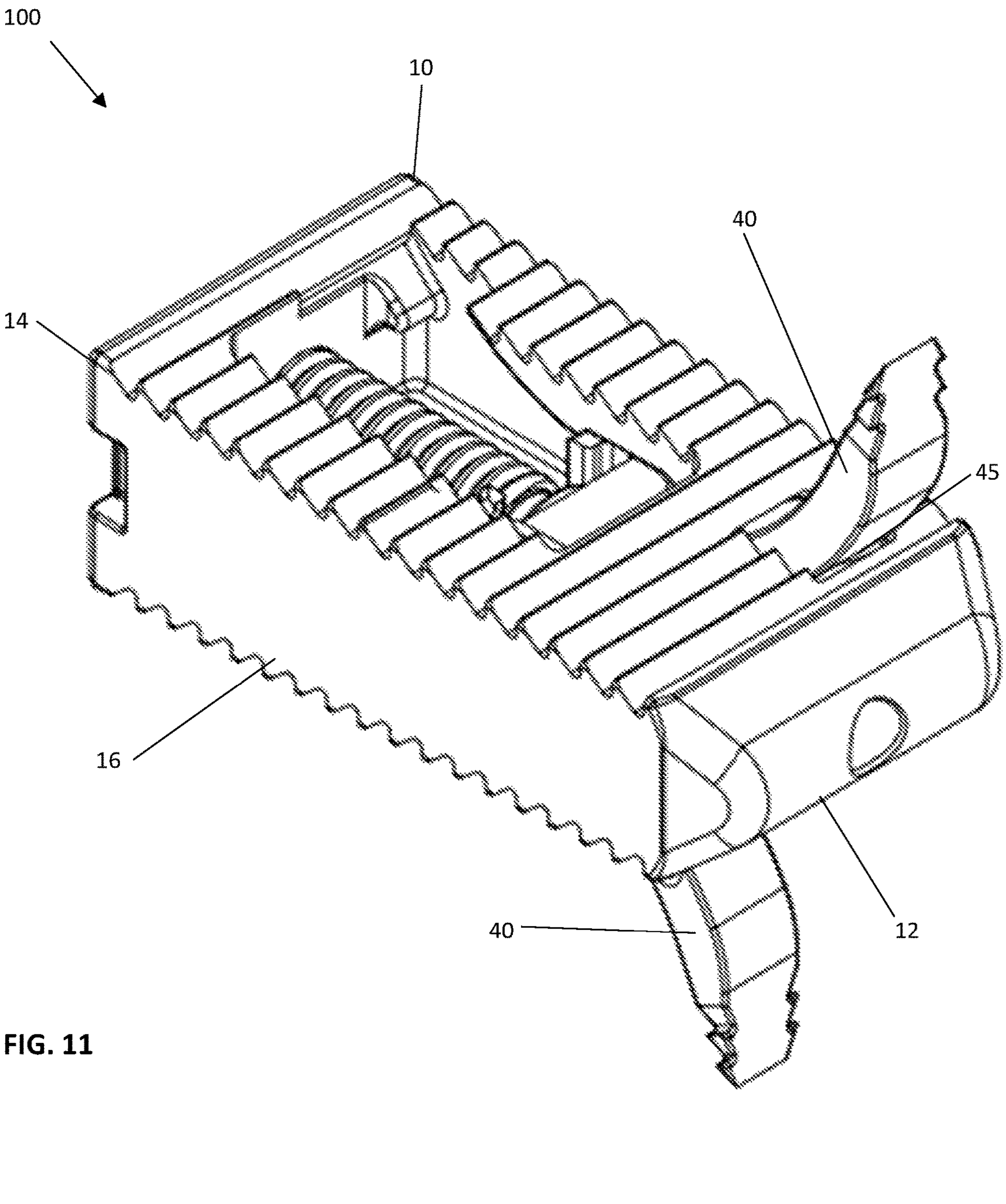
FIG. 11 is perspective view of the SI fusion device in a deployed position.
Figure 12:
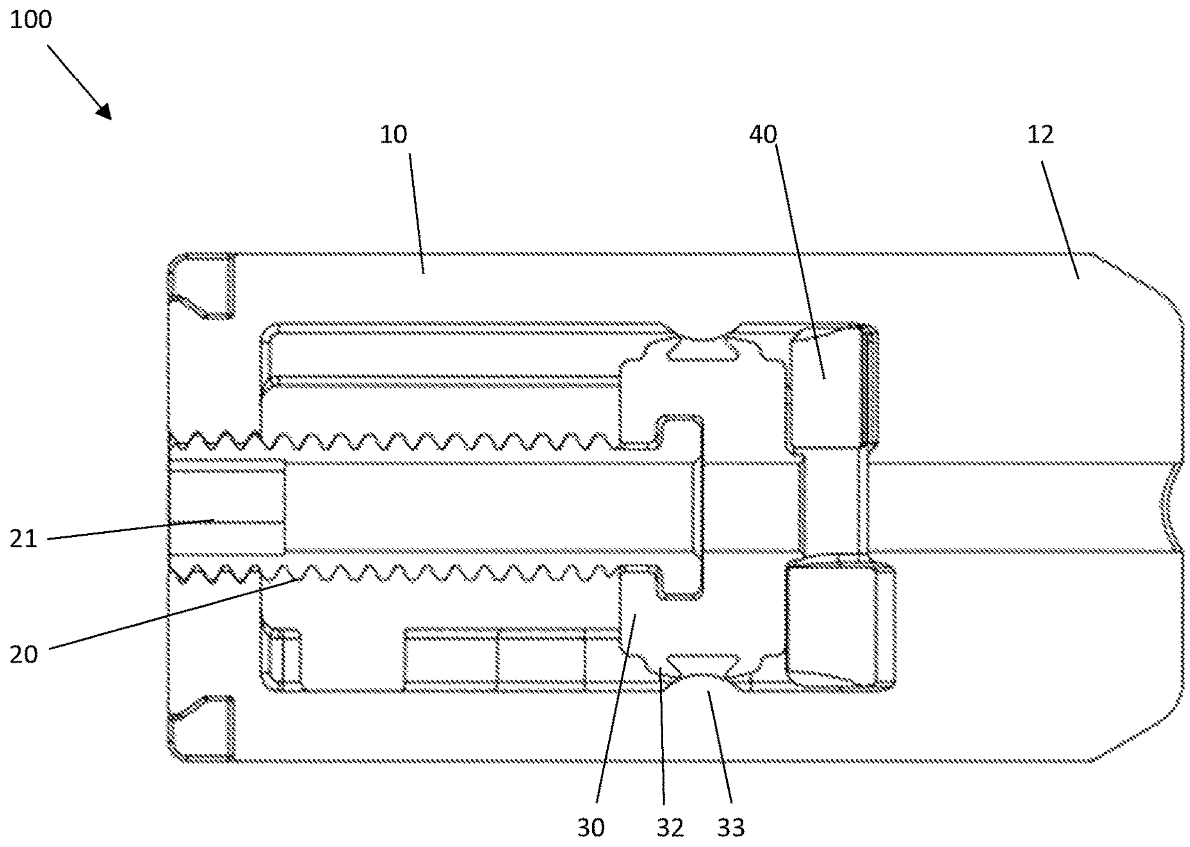
FIG. 12 is a cross-sectional view of the SI fusion device in a deployed position.

FIG. 11 shows the spikes 40 fully extended and having a curvilinear shape such that as the spikes 40 are pushed forward, they follow a curvilinear path. As shown, the pockets 45 on the implant body 10 are on a first exterior surface 15 allowing a first spike 40 to extend outwardly therefrom and similarly on a second opposite exterior surface 16 has a pocket 45 such that the second spike 40 can be pushed in an opposite direction relative to the implant body 10. Each of these pockets 45 are spaced between the longitudinal axis and a side of the implant body 10 as illustrated.

Figure 13:
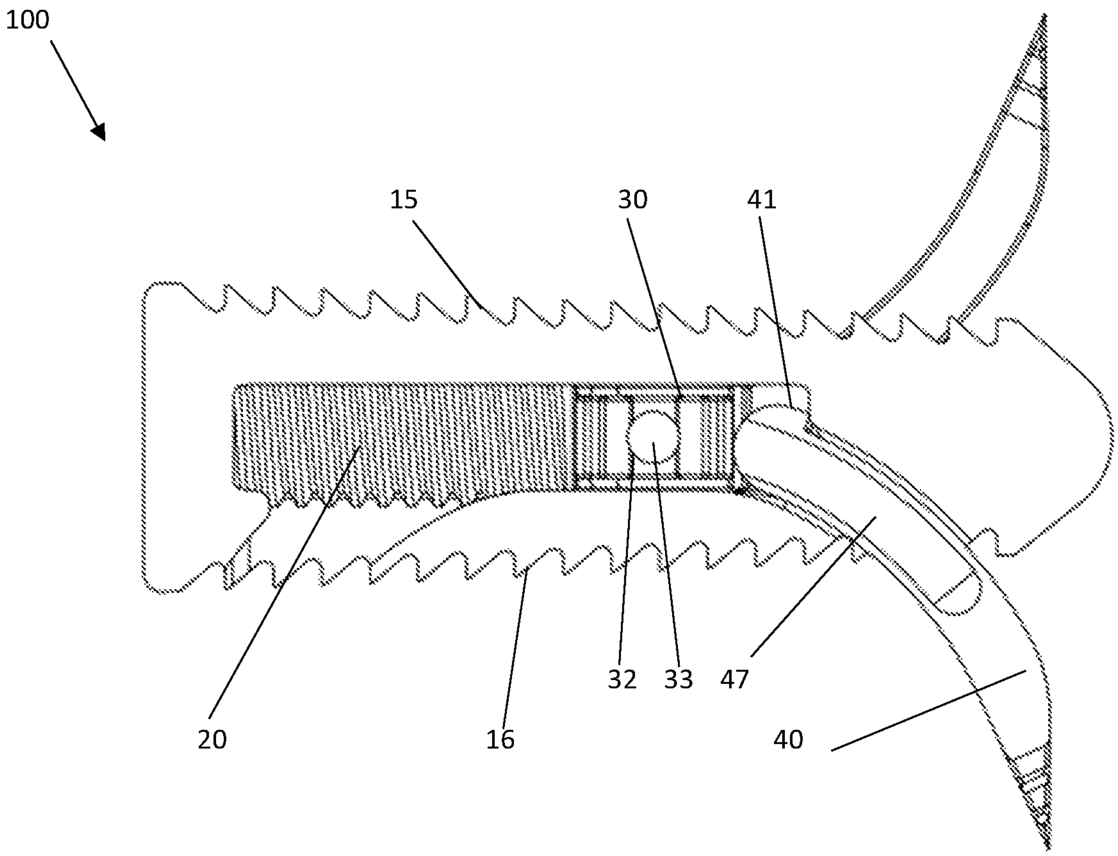
FIG. 13 is a cross-sectional view of the SI fusion device in a deployed position.

FIG. 13 is a cross-sectional view showing the threaded post 20 in the fully threaded position with the spikes 40 in the extended or deployed position. As shown, the threaded post 20 has a hexagonal end 21 upon which a tool can be inserted to provide the rotation necessary to move the device 100. FIG. 13 shows this in greater detail.

It is important to note that the sliding block assembly 30 moves directly to an end wherein the sliding block 30 has a pair of cleats 32 on each side that when the block 30 is moved to the fully extended position towards the distal end, these cleats 32 straddle and align with protrusions 33 on each side of the implant body 10 creating a stop to help prevent the spikes from being moved back to the retracted position. Additionally, each spike 40 has a positive internal stop 41 which prevents the spike from being able to pass out of the implant body 10 in the fully extended position as best shown in FIG. 13.

Various components of the implant device assembly 100 can be made under numerous manufacturing techniques including machining and 3D printing. The implant body 10 may be made of a metal material or synthetic polymer such as PEEK. In either case, the sliding block 30 similarly may be made of such materials. It is recommended that the threaded post 20 be of a high strength metal material such as titanium or stainless steel. All the materials must be implantable for use an as implant in the implant device assembly.

Variations in the present invention are possible in light of the description of it provided herein. While certain representative embodiments and details have been shown for the purpose of illustrating the subject invention, it will be apparent to those skilled in this art that various changes and modifications can be made therein without departing from the scope of the subject invention. It is, therefore, to be understood that changes can be made in the particular embodiments described which will be within the full intended scope of the invention as defined by the following appended claims.

What is claimed is:

1. A sacroiliac fusion implant device assembly, the device assembly comprising:

an implant body, the implant body having a distal end and a proximal end with a longitudinal axis extending between a center of the distal end and a center of the proximal end, the distal end having a tapered end with an opening configured to receive a guide pin during insertion into a joint between a sacrum and an ilium, and the proximal end having a cannulated threaded post configured to receive the guide pin and to move a sliding block;

a pair of sidewalls connecting the distal and proximal ends;

a sliding block positioned in the implant body and held to the threaded post, wherein the sliding block being movable from a retracted unlocked position and to a deployed locked position when moved toward the distal end as the threaded post is rotated clockwise;

a pair of movable bone spikes held in opposing sides of the implant body, wherein each bone spike being held in a pocket of the implant body, wherein a first pocket is open at a first surface of the implant body and a second pocket being open at an opposing second surface of the implant body, wherein the bone spikes are movable from a retracted position in the implant body to an exposed deployed locked position by moving the sliding block which presses the spikes up and out of the retracted position extending the bone spikes into bone in the sacroiliac joint; and a pair of locking cleats on the sliding block engaging sidewalls of the implant body when the threaded post is rotated into the implant body proximal end, wherein the locking cleats of the sliding block is aligned with a protrusion on the sidewall of the implant body to help prevent the bone spikes from being moved back to the retracted position and to provide an indication that the threaded post has reached the fully inserted position with the bone spikes deployed.

2. The sacroiliac fusion implant device assembly of claim 1, wherein each of the bone spikes has a curved groove extending along a portion of the side of the bone spike that moves over the protrusion following a curvilinear path to the deployed locked position as the sliding block presses against the bone spike.

3. The sacroiliac fusion implant device assembly of claim 1, wherein each of the pair of bone spikes is curvilinear and has a positive stop at the proximal end of the bone spike to prevent over deployment.

4. The sacroiliac fusion implant device assembly of claim 1, wherein the first exterior surface and the second exterior surface have a plurality of gripping ridges configured to engage bone or tissue upon implantation.

5. The sacroiliac fusion implant device assembly of claim 4, wherein the plurality of gripping ridges are inclined from the distal end towards the proximal end at an angle of 45 degrees or less.

6. The sacroiliac fusion implant device assembly of claim 1, wherein the implant body is manufactured by traditional machining techniques or 3D printed using implantable grade materials.

7. The sacroiliac fusion implant device assembly of claim 1, wherein the implant body is made of titanium.

8. The sacroiliac fusion implant device assembly of claim 1, wherein the implant has dimensions of 9 mm height, 14 mm width and 28 mm length at the distal end with a range of a 0 degree to 7 degree inclination toward the proximal end.

9. The sacroiliac fusion implant device assembly of claim 1, wherein the implant may be offered in a reusable or disposable instrument/implant set.

* * * * *